(12) United States Patent
Heublein et al.

(10) Patent No.: US 8,771,751 B2
(45) Date of Patent: Jul. 8, 2014

(54) METALLIC IMPLANT WHICH IS DEGRADABLE IN VIVO

(75) Inventors: Bernd Heublein, Hannover (DE); Gerd Hausdorf, Wettmar (DE)

(73) Assignee: Biotronik AG (CH)

( * ) Notice: Subject to any disclaimer, the term of this patent is extended or adjusted under 35 U.S.C. 154(b) by 235 days.

(21) Appl. No.: 13/211,921

(22) Filed: Aug. 17, 2011

(65) Prior Publication Data

US 2011/0301694 A1 Dec. 8, 2011

Related U.S. Application Data

(63) Continuation of application No. 12/897,967, filed on Oct. 5, 2010, now abandoned, which is a continuation of application No. 09/269,084, filed as application No. PCT/EP98/04415 on Jul. 17, 1998, now Pat. No. 7,879,367.

(30) Foreign Application Priority Data

Jul. 18, 1997 (DE) .................................. 197 31 021

(51) Int. Cl.
*A61K 33/26* (2006.01)
*A61F 2/82* (2013.01)

(52) U.S. Cl.
USPC ........... 424/646; 424/426; 424/617; 424/655; 623/1.15; 623/1.38

(58) Field of Classification Search
None
See application file for complete search history.

(56) References Cited

U.S. PATENT DOCUMENTS

| 2,094,578 A | 10/1937 | Blumenthal et al. |
| 5,843,172 A | 12/1998 | Yan |
| 5,980,252 A * | 11/1999 | Samchukov et al. ......... 433/215 |
| 7,879,367 B2 | 2/2011 | Heublein et al. |

FOREIGN PATENT DOCUMENTS

WO WO 9903515 A2 * 1/1999

* cited by examiner

*Primary Examiner* — Abigail Fisher
*Assistant Examiner* — Frank Choi
(74) *Attorney, Agent, or Firm* — Brannon Sowers & Cracraft PC; Edward E. Sowers

(57) ABSTRACT

The invention relates to a medical implant made of a metallic material. After fulfilling its temporary support function, the implant is degraded by corrosion at a predetermined rate. Negative long-term effects are thus avoided.

6 Claims, No Drawings

METALLIC IMPLANT WHICH IS DEGRADABLE IN VIVO

CROSS-REFERENCES TO RELATED APPLICATIONS

This application is a continuation of application Ser. No. 12/897,967, filed on Oct. 5, 2010, now abandoned, which is also a continuation of application Ser. No. 09/269,084, filed on Nov. 29, 1999, which issued as U.S. Pat. No. 7,879,367, and which is a National Stage filing of International Application PCT/EP98/04415, filed Jul. 17, 1998, claiming priority to German Application No. DE 197 31 021.4 filed Jul. 18, 1997.

BACKGROUND OF THE INVENTION

1. Field of the Invention

The present invention relates to implants made of metallic materials for use in the human or animal body.

2. Description of Related Art

Implants of this type hare in principle been known for a long time. The first implants were developed for orthopaedic purposes, for example screws and nails for fixing bone fractures. These initially consisted of relatively simple iron alloys which were prone to corrosion under in vivo conditions. The corrosion led to metals being released as ions in the direct vicinity of the bone providing an unwanted stimulus for the growth of bone tissue. The bone grew more than is actually wanted and necessary. This led to damage to healthy bone material.

For this reason, attempts have been made to fabricate metallic implants in principle from materials with maximum corrosion resistance. Currently in use in this connection are mainly corrosion-resistant stainless steels, tantalum and titanium. These implants persist as foreign bodies after the implantation and they are recognized as such by the body. They can be removed only by a second operation.

In addition, metallic implants are known in the specialty of vascular surgery and cardiology, angiology and radiology. These implants comprise, for example, endoluminal and vessel supports (stents) for treating lesions. These supports are used, for example, for widening and maintaining the lumen of narrowed vessels by keeping the vessel lumen at an appropriately optimal internal diameter using a balloon catheter (balloon expandable) or self-expanding from the vessel lumen outwards. The implant is intrinsically necessary only until the diseased vessel is able permanently to maintain the necessary diameter under its own power due to biological repair processes. This is generally the case about 4 weeks after implantation.

However, some disadvantages are associated with permanent retention of a metallic implant. As a foreign body, the implant leads to local and possibly also systemic reactions. In addition, the self-regulation of the affected vessel segment is impeded. The continual (pulsatile) stress on the metal may lead to fatigue fractures, which in the case of large-lumen implants (e.g. occlusion systems such as umbrellas) may lead to new medical problems. About 20% of vessel supports in smaller lumina (2.5-6 mm) cause renewed stenosis (called in-stent stenosis) which, given the large number of implants, accumulates to an additional medical and economic burden. In some vessel regions (e.g. extracranial vessels, leg arteries) the metallic structure may be permanently deformed by forces acting from outside, resulting in renewed vessel obstruction or induced vessel occlusion. Every permanent implant is additionally associated with problems in particular for younger patients because retention for decades is unavoidable.

The only completely biodegradable implants disclosed to date, for example in DE 2502884 C2, are made of synthetic materials. There is disclosure therein of coating an orthopaedic implant with polymethylmethacrylate which is biodegradable. Other synthetic materials comprise polylactide and polyglycolic esters. In addition, EP 0006544 B1 discloses a biodegradable ceramic material based on calcium phosphate, which is likewise used for coating metallic implants.

Finally, WO 81/02668 discloses an orthopaedic implant which comprises a corrosion-resistant metallic basic component and a biodegradable intermediate metallic layer for the bone contact region. This intermediate layer forms together with the basic component an electrochemical cell and generates an electrical voltage which promotes bone growth. At the same time, the surface layer which may, for example, consist of silver alloys is degraded. This leads to the desired effect, that bone growth is beneficially influenced for as long as necessary and then, after complete degradation of the surface coating, the electrical stimulus declines.

Previously disclosed biodegradable polymer-based substances are used in vascular surgery. Their mechanical properties on the one hand and the subsequent foreign-body reaction during the biodegradation on the other hand lead to them is being unsuitable on their own as material for implantation. Metallic materials/alloys have favourable mechanical properties (elasticity, deformability, while being less bulky, which is an important precondition for administration through thin-lumen guide systems in the transcutaneous procedure.

SUMMARY OF THE INVENTION

It is therefore an object of the present invention to provide implants made of biodegradable material having at the same time advantageous mechanical properties.

This object is achieved by a medical implant made of metallic material, characterized in that the material is degradable in vivo through corrosion.

Because the medical implant is fabricated from a metallic material which is degradable in vivo through corrosion, in the first place the mechanical advantages of metallic materials are present. The corrosive degradation of the implant within a time scale which can be set by the choice of material prevents, on the other hand, the adverse long-term effects of the metallic foreign body occurring. It is moreover biologically advantageous if the material is pure iron, where appropriate with a content of up to 7% carbon or an alloy or a sintered metal, the main constituent of which is selected from the group of alkali metals, of alkaline earth metals, iron, zinc or aluminium. Magnesium or iron is currently preferred as main constituent.

The biological, mechanical and chemical properties of the materials can be beneficially affected if a subsidiary constituent is provided in the form of manganese, cobalt, nickel, chromium, copper, cadmium, leads tin, thorium, zirconium, silver, gold, palladium, platinum, rhenium, silicon, calcium, lithium, aluminium, zinc, iron, carbon or sulphur. The material preferred overall at present is either an alloy of magnesium with a content of up to 40% lithium plus addition of iron, or an iron alloy with a small content of aluminium, magnesium, nickel and/or zinc.

Corrosion which is particularly satisfactory at the start of the degradation period is afforded by an alloy or a sintered metal made of approximately equal parts of zinc and irons.

Advantageous decomposition times have furthermore been afforded by materials with magnesium as main constituent and either

- 0-40% lithium, 0-5% iron and less than 5% other metals or rare earths;
- 2-5% aluminium, 0-12% lithium and 1-4% rare earths, in particular cerium, lanthanum, neodymium and/or praseodymium,
- 6-17% lithium, 2% aluminium and 1% rare earths,
- 0-8% lithium, 2-4% aluminium and 1-2% rare earths,
- 8.5-9.5% aluminium, 0.15%-0.4% manganese, 0.45-0.9% zinc
- 4.5-5.3% aluminium, 0.28%-0.5% manganese or
- 30-40% lithium and 0-5% other metals and/or rare earths.

Magnesium alloys of these types are available, for example, under the names AZ91D, AM50A and AE42.

The design of the medical implant has several basic variants. The basic component provided for a vessel support is a tubular structure with additional processing. Advantageous occlusion systems (e.g. ductus arteriosus, congenital and acquired septal defects, arteriovenous shunt connections) are passively and/or actively unfoldable umbrella forms, helices or complex components. The invention is also applicable to occluders as systems for occluding connections between cavities, vessels or duct systems.

It is additionally advantageous to provide the implant as fastening or supporting device for temporarily fixing tissue parts in the form of implants or transplants.

To adjust the rate of corrosion of the material, it is advantageous if the thickness of the material is chosen as a function of the composition of the materials so that the degradation or corrosion process in vivo is essentially complete in between 5 days and 6 months, in particular between 2 weeks and 8 weeks.

This results in the fixing device, which is no longer necessary, disappearing after the tissue implant has taken.

Finally, it is advantageous if the implant is designed as orthopaedic implant, as implant for dentistry, for surgery to the upper abdomen or for accident surgery, in particular for treating the human body, in which case the alloy must be chosen so that bone growth is not adversely or excessively influenced. Orthopaedic implants according to the invention in the form of nails, screws or plates can be designed to degrade after the treated bone fracture has set and not require removal in a second operation.

Various exemplary embodiments of the present invention are indicated below.

EXAMPLE 1

Vessel Support

A stent according to the invention is fabricated from a tubular basic component of the metallic material and subsequent processing. The mechanical structure of stents of this type is known, for example, from EP 0221570 B1, in which case the material is, however, a corrosion-resistant stainless steel.

In this example of the stent according to the invention, the material is either an alloy having magnesium as main constituent and, where appropriate, the subsidiary constituents lithium, iron, zinc and traces of nickel, or an alloy having iron as main constituent and the subsidiary constituents chromium and nickel plus, where appropriate, traces of other additions. The percentage composition of the magnesium alloy should be approximately in the region of 50-98% magnesium, 0-40% lithium, 0-5% iron and less than 5% other metals, and that of the iron alloy approximately in the region of 88-99% iron, 0.5-7% chromium and 0.5-3.5% nickel plus less than 5% other metals. The wall thickness of the stent struts should be between 50 and 100 µm after the processing.

In practice, the stent according to the invention will be inserted in a manner known per se using a balloon catheter into a pathologically narrowed blood vessel and there dilated or released as self-expanding stent, in which case it keeps the blood vessel at the required diameter. A restenosis remaining without stent implantation (recoil) and/or a tissue tear induced by the dilatation are effectively treated. Within 2-4 weeks the stent is covered by intimal tissue and initially retains its supporting function. The blood vessel acquires a new intrinsic stability through tissue growth as a result of its own repair processes in the region of the implanted stent. The vessel lumen is stabilized at an optimal level. The choice of the alloy material together with the chosen watt thickness result, on the other hand, in the stent gradually being degraded in the wall of the blood vessel and being present only in traces after 4-12 weeks. The disadvantages of a permanent implant are decreased or eliminated by the present invention. Such disadvantages include local and possibly systemic reactions, impedance of the self-regulation of the affected vessel segment, stress on the metal due to pulsations leading to fatigue fractures and, in the case of large-lumen implants including occlusion systems such as umbrellas, may lead to new medical problems.

EXAMPLE 2

Occlusion System

An occlusion system (umbrella) according to the invention is fabricated from a metallic skeleton to which a plastic umbrella is affixed. Umbrellas of this type are known, for example made of the alloy MP35N or Nitinol. Occlusion Systems of this type are used to occlude defects in septa of the heart. The wall thickness of the metallic framework is about 500 mm. In practice, the umbrella is folded up in a manner known per se and released in the defect which is to be occluded. Within 3-4 weeks, the umbrella is covered by endogenous tissue and acquires a new intrinsic stability thorough this tissue growth. The choice of the alloy material together with the tissue wall thickness results in the metallic framework being degraded within 4 weeks to a few months and being presently in traces after one year. The plastic content of the umbrella remains, which is not critical because of the flexibility of the material. The degradation of the metallic portion has the advantage by comparison with known umbrellas that, even if there are unpredicted stresses, e.g. associated with traffic accidents, there is no longer a risk of vessel walls being pierced. Moreover the advantage according to the invention is achieved even if the degradation results initially in mechanical instability of the framework.

EXAMPLE 3

Helix for Occluding Vessels (Occluder)

A helix (coil) according to the invention is fabricated from a metallic material wound helically, and the helix is prefixed. The diameter of the initial winding is 0.1-1 mm depending on the vessel to be occluded. Helices (coils) of this type are known, for example made of Nitinol, platinum alloys or tungsten alloys.

In the present embodiment according to the invention, the material is an alloy with iron as main constituent and with subsidiary constituents nickel and/or chromium and traces of magnesium and zinc.

In practice, the occluding helix (coil) is inserted in the extended state in a cardiac catheter in a manner known per se and is advanced through the latter as far as the vessel to be occluded. When the helix is released from the cardiac catheter it resumes its previous shape and occludes, through its lumen and its thrombogenicity, which can be increased by Dacron or other fibres, the vessel to be occluded. After the vessel has thrombosed and connective tissue has grown in, the occlusion mechanism acquires a new intrinsic stability. The administered helix is gradually degraded so that only traces of the implanted material are still present after about one year.

The exemplary embodiments mentioned above can be fabricated both with use of magnesium alloys and with use of iron alloys. The materials are not known to have toxic effects at the concentrations to be expected.

Magnesium alloys have the advantage that it is possible to select very accurately the degradation rate to be expected in vivo by a suitable choice of the other alloy constituents. In addition, magnesium is physiologically very well tolerated. Iron alloys are advantageous in terms of the mechanical stability, which is manifested by the small wall thicknesses possible for the implants. The alloy material can therefore be selected depending on the case for which it is used.

In one aspect, the present invention provides medical implants which are made of a metallic material, characterized in that the material is degradable in vivo through corrosion. Metallic materials from which implants of the invention can be made are characterized in that the primary material is pure iron or an alloy whose main constituent is selected from the group comprising the following: alkali metals, alkaline earth metals, iron, zinc, aluminium. In a further aspect, the primary metallic material from which implants of the invention can be made is further characterized in that the material contains magnesium, iron, or zinc as main constituent. In one preferred embodiment, a medical implant according to the invention is characterized in that the metallic material contains iron and 0.5 to 7% carbon. In another aspect, a medical implant according to the invention is characterized in that the metallic material contains iron and zinc in approximately the same concentration.

In an additional aspect, a medical implant according to the invention is characterized in that the metallic material contains as subsidiary constituents one or more elements from the group comprising the following: Mn, Co, Ni, Cr, Cu, Cd, Ph, Sn, Th, Zr, Ag, Au, Pd, Pt, Re, Si, Ca, Li, Al, Zn, Fe, C, S. In some preferred embodiments, the metallic material contains 50-98% magnesium, 0-40% lithium, 0-5% iron and less than 5% other metals or rare earths. In other preferred embodiments, the metallic material contains 79-97% magnesium, 2-5% aluminium, 0-12% lithium and 1-4% rare earths, in particular cerium, lanthanum, neodymium and/or praseodymium. In yet other preferred embodiments, the alloy is characterized in that the material contains 85-91% magnesium, 12% lithium, 2% aluminium and 1% rare earths. In yet other embodiments, the metallic material contains 86-97% magnesium, 0-8% lithium, 2% 4% aluminium and 1-2% rare earths.

In additional preferred embodiments, the metallic material contains 8.5-9.5% aluminium, 0.15%-0.4% manganese, 0.45-0.9% zinc and the remainder to 100% magnesium. In still other preferred embodiments, the metallic material of a medical implant according to the invention is characterized in that the material contains 4.5-5.3% aluminium, 0.28%-0.5% manganese and the remainder to 100% magnesium. In additional preferred embodiments, the metallic material is characterized in that the material contains 55-65% magnesium, 30-40% lithium and 0-5% other metals and/or rare earths. In yet additional preferred embodiments, the metallic material is characterized in that the material contains 88-99.8% iron, 0.1-7% chromium and 0-3.5% nickel plus less than 5% other metals or the material contains 90-96% iron, 3-6% chromium and 0-3% nickel plus 0-5% other metals.

In another key aspect, a medical implant according to the present invention is characterized in that the implant is a vessel support having an essentially tubular basic component. Preferred shapes for an implant of the invention include a helix (coil), and umbrella, a stent, a wire network, a clip or a plug, in an additional key aspect, a medical implant according to the present invention is characterized in that the implant has an endoluminal supporting function in hollow organs and/or duct systems (e.g. ureters, bite ducts, urethra, uterus, bronchi). In another significant aspect, a medical implant according to the present invention is characterized in that the implant is an occlude useful in a system for occluding connections between cavities, vessels or duct systems, or the implant is a fastening or supporting device for temporarily fixing tissue implants or transplants. In still other significant embodiments, a medical implant of the invention includes an orthopaedic implant, for example, a screw, a nail, a wire, a plate or a part of a joint.

As a further advantage, a medical implant according to the present invention includes those where the thickness of the material is chosen as a function of the composition of the material so that the degradation or corrosion process in vivo is essentially complete within the time period, or region, of 5 days up to 6 months, in particular between 2 weeks and 8 weeks. As another advantageous aspect, the thickness of the material is chosen as a function of the composition of the material so that the degradation or corrosion process in vivo is essentially complete within the region of 6 months up to 10 years, in particular between 1 year and 5 years. Preferably, the metallic material composition, thickness and other dimensions are chosen so that the degradation or corrosion process in vivo initially leads to mechanical instability of the implant shape before the degradation process of the metallic material is essentially complete.

We claim:

1. A device comprising a medical implant made from a metallic material degradable in vivo through corrosion,
   wherein the material has a thickness and a composition consisting of an alloy having iron as its major constituent,
   wherein the material contains 88-99.8% iron, 0.1-7% chromium, 0-3.5% nickel, and less than 5% other metals, and, optionally, up to 7% carbon,
   wherein the implant is a vascular support in the form of a stent.

2. The device of claim 1, wherein the material further contains up to 7% carbon.

3. The device of claim 1, wherein the thickness of the material is selected with regard to the composition of the material in order to provide substantially complete degradation or corrosion of the device in vivo within from about 5 days to about 6 months.

4. The device of claim 1, wherein the thickness of the material is selected with regard to the composition of the material in order to provide substantially complete degradation or corrosion of the device in vivo within from about 2 weeks to about 8 weeks.

5. The device of claim 1, wherein the thickness of the material is selected with regard to the composition of the material in order to provide substantially complete degradation or corrosion of the device in vivo within from 6 months to 10 years.

6. The device of claim 1, wherein the thickness of the material is selected with regard to the composition of the material in order to provide substantially complete degradation or corrosion of the device in vivo within from about 1 year to about 5 years.

* * * * *